United States Patent [19]

Pappo et al.

[11] 3,969,391

[45] July 13, 1976

[54] PREPARATION OF PROSTAGLANDIN PRECURSORS

[75] Inventors: Raphael Pappo, Skokie; Christopher Jung, Morton Grove, both of Ill.

[73] Assignee: G. D. Searle & Co., Chicago, Ill.

[22] Filed: May 8, 1974

[21] Appl. No.: 467,847

Related U.S. Application Data

[63] Continuation-in-part of Ser. No. 249,667, May 2, 1972, abandoned.

[52] U.S. Cl. .................. 260/468 K; 260/410.9 R; 260/413; 260/468 D; 260/514 D; 260/514 K
[51] Int. Cl.$^2$ .......................................... C07C 51/00
[58] Field of Search ........ 260/468 D, 468 K, 514 D, 260/514 K

[56] References Cited

FOREIGN PATENTS OR APPLICATIONS

| 2,187,754 | 1/1974 | France | 260/468 |
| 2,321,984 | 11/1973 | Germany | 260/468 |

*Primary Examiner*—Robert Gerstl
*Attorney, Agent, or Firm*—John A. Dhuey

[57] ABSTRACT

2-Alkoxy-4-hydroxy-5-oxocyclopent-1-eneheptanoic acid and its lower alkyl esters are reduced with metallic hydrides to yield the corresponding 3-hydroxy-5-oxo-cyclopent-1-eneheptanoic acid and its esters. The latter compounds are valuable intermediates in the preparation of pharmacologically active prostaglandin derivatives.

10 Claims, No Drawings

PREPARATION OF PROSTAGLANDIN PRECURSORS

This application is a continuation-in-part of our co-pending application Ser. No. 249,667, filed May 2, 1972 now abandoned.

The invention described herein generally relates to a process for the manufacture of cyclopentane-alkanoic acids and esters. In particular, the present invention relates to a novel process for the production of 3-hydroxy-5-oxocyclopent-1-enealkanoic acids and their esters of the following structural formula

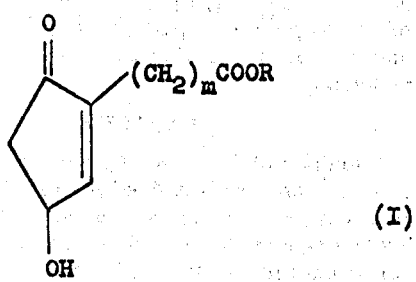

wherein R is hydrogen or a lower alkyl radical and $m$ is an integer greater than 4 and less than 8. The instant process is practiced by reducing a compound of the formula

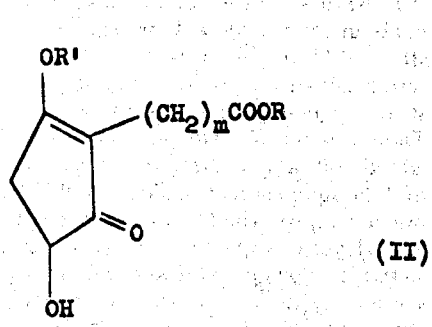

wherein R and $m$ are defined as above and R' is a lower alkyl radical, with a hydride reducing agent in a suitably inert solvent and contacting the unisolated 5-hydroxy enol ether intermediate with a suitable acidic agent which effects hydrolysis and dehydration thus forming the corresponding compounds of formula I.

The lower alkyl radicals represented by R and R' in the above formulas contain, inclusively, 1–7 carbon atoms and are illustrated by methyl, ethyl, propyl, butyl, pentyl, hexyl, heptyl and the branched-chain radicals isomeric therewith.

The hydride reducing agents useful in the instant process are represented by the structural formulas

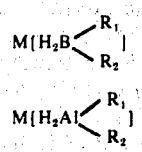

wherein M is an alkali metal as illustrated by sodium, potassium and lithium and $R_1$ and $R_2$ are hydrogen, lower alkyl or lower alkoxy. Illustrative of those compounds are sodium borohydride, potassium borohydride, lithium borohydride, lithium aluminum hydride, sodium aluminum hydride and sodium dihydro bis(2-methoxyethoxy)aluminate. Also useful as reducing agents are aluminum hydride, borane and zinc borohydride. Of the above compounds, the aluminum hydrides are preferred, with sodium dihydro bis(2-methoxyethoxy)aluminate being particularly preferred.

The lower alkyl radicals represented by $R_1$ and $R_2$ comprehend those radicals having 1–7 carbon atoms inclusive as illustrated by methyl, ethyl, propyl, butyl, pentyl, hexyl, heptyl and the branched-chain isomers thereof. The lower alkoxy radicals represented by $R_1$ and $R_2$ include those of the formula $R_3$—O— or of the formula $R_4$—O—$R_5$—O—, i.e. (lower alkoxy) lower alkoxy wherein $R_3$, $R_4$ and $R_5$ are lower alkyl radicals as defined above. Illustrative of the alkoxy radicals intended are methoxy, ethoxy, propoxy, methoxyethoxy and methoxypropoxy.

Effective acidic agents for use in the hydrolysis-dehydration step are illustrated by the mineral acids such as hydrochloric acid, sulfuric acid, nitric acid and perchloric acid and the strong organic acids but not limited thereto.

Typical inert solvents are illustrated by tetrahydrofuran and toluene. The choice of solvents is generally determined by solubility considerations which will be well-known to those skilled in the art. The process is run at low temperatures with a temperature range of between about −90°C. to +10°C. being illustrative. However, when the ester moiety is not present in the compounds of formula (II), it is not necessary that the process be run at low temperatures. For example, the process then can be run at temperatures up to 100°C. Reaction times are acritical, with times of between 1 to 16 hours being typical.

The compounds produced by the instant process are isolable by extraction and chromatographic methods which are known in the art. For example, extractions with ethyl acetate and chromatographic separation on silicic acid with ethyl acetate-benzene as eluant are typical.

In a preferred embodiment of this invention, 2-methoxy-4-hydroxy-5-oxocyclopent-1-eneheptanoic acid and its lower alkyl esters are allowed to react with an aluminum hydride reducing agent and then with a mineral acid to afford the corresponding 3-hydroxy-5-oxocyclopent-1-eneheptanoic acid and its esters.

In an especially preferred embodiment of this invention, 2-methoxy-4-hydroxy-5-oxocyclopent-1-ene-heptanoic acid and its lower alkyl esters are reduced with sodium dihydro bis(2-methoxyethoxy)aluminate and then contacted with aqueous hydrochloric acid to yield 3-hydroxy-5-oxocyclopent-1-eneheptanoic acid and its esters, respectively.

The starting materials which are employed in the practice of the instant process are prepared by methods described by Pappo, Collins and Jung, *Annals N.Y. Academy of Sciences*, 180, 64 (1971). For example, 2-methoxy-4-hydroxy-5-oxocyclopent-1-eneoctanoic acid and its lower alkyl esters are prepared by the methods described therein by substituting 10-oxoundecanoic acid in place of the 9-oxodecanoic acid used as starting material. Furthermore, the 2-alkoxy derivatives are prepared by substituting the appropriate 2,2-di(lower alkoxy)propane in place of the 2,2-dimethoxypropane reagent and by substituting the corresponding alkanol solvent for the methanol solvent described therein.

Typical of the claimed process is the treatment of a solution of methyl 2-methoxy-4-hydroxy-5-oxocyclopent-1-eneheptanoate in toluene with a toluenic solution of sodium dihydro bis(2-methoxyethoxy)aluminate at a temperature of −70°C. to −60°C., followed by warming to 0°C. and treatment of the unisolated methyl 4,5-dihydroxy-2-methoxycyclopent-1-eneheptanoate with aqueous hydrochloric acid, thereby affording methyl 3-hydroxy-5-oxocyclopent-1-eneheptanoate.

The compounds produced by the instant process are useful in the preparation of pharmacologically active prostaglandin derivatives which exhibit anti-ulcerogenic and prostaglandin antagonist activity. For example, methyl 3-hydroxy-5-oxocyclopent-1-eneheptanoate is allowed to react with trans-1-hexenyl copper to produce methyl 3-hydroxy-2-(1-hexenyl)-5-oxocyclopentaneheptanoate. That compound possesses antiulcerogenic activity as is determined by an assay described in U.S. Pat. No. 3,483,192. When trans-1-octenyl copper is employed, there is obtained methyl 3-hydroxy-2-(1-octenyl)-5-oxocyclopentaneheptanoate, that compound displaying prostaglandin antagonist activity.

The prostaglandin antagonist activity is demonstrated in the following procedure which is substantially the same as that described by J. H. Sanner, *Arch. int. Pharmacodyn.*, 180 (1), 46 (1969):

Female albino guinea pigs weighing 200–500 g. are sacrificed by cervical dislocation and the ileum is quickly removed and placed in modified Tyrode solution containing ½ the usual amount of magnesium ions. Segments of ileum, about 2 centimeters long, are cut and mounted in a 2 or 4 ml. tissue bath containing the modified Tyrode solution. The solution is maintained at 37° and bubbled with a gaseous mixture of 95% oxygen and 5% carbon dioxide. Contractions are detected isotonically. Approximately equal submaximal contractions are obtained in preliminary trails by adjusting the doses of prostaglandin $E_2(PGE_2)$ added to the bath. Two control contractions are obtained at 3.5 minute intervals. A solution or suspension of the test compound in the bathing solution is then substituted for the original modified Tyrode solution. The test suspension is kept in constant contact with the tissue for the remainder of the experiment except for brief periods to drain the bath in preparation for rinsing with fresh test suspension. Three more contractions are elicited to the agonist in the presence of the test compound without interrupting the time sequence. The last two sets of treated responses are compared with the two sets of control responses. The first set of treated responses is not used for comparisons, being used only to maintain the timed sequence of injections during the period allowed for the tissue to become equilibrated with the antagonist. A compound is rated active if the mean of contractions produced by any agonist is reduced 75% or more by the test compound.

Sih, et al. *J.C.S. Chem. Comm.*, No. 4, 240(1972) report the preparation of (±)-15-deoxy-PGE$_1$ from ethyl 3-hydroxy-5-oxocyclopent-1-eneheptanoate. The former compound displays PGE$_1$-like activity when tested in a guinea pig tracheal strip assay.

The trans-1-alkenyl copper compounds used in the above procedures are prepared by a sequence of steps which begins with the contacting of 1-alkynes with catechol borane. The product that forms is treated with mercuric chloride and the trans-1-alkenyl mercuric chloride thus produced is contacted with magnesium, activated with mercuric chloride, to afford the trans-1-alkenyl magnesium chlorides. Those compounds are allowed to react with cuprous iodide in an appropriate solvent such as tetrahydrofuran to afford the trans-1-alkenyl copper derivatives, which preferably are employed in situ.

The invention will appear more fully from the examples which follow. Those examples are given by way of illustration only and are not to be construed as limiting the invention either in spirit or in scope as many modifications both in materials and methods will be apparent to those skilled in the art. Temperatures are given in degrees Centigrade (°C.) and quantities of material in parts by weight unless parts by volume is specified. The relationship between parts by weight and parts by volume is the same as that existing between grams and milliliters.

EXAMPLE 1

A solution of 15.5 parts by volume of a 1.83 M sodium dihydro bis(2-methoxyethoxy)aluminate in benzene solution in 87 parts of toluene and a solution of 6.92 parts of methyl 2-methoxy-4-hydroxy-5-oxocyclopent-1-eneheptanoate in 176 parts of toluene are simultaneously added, dropwise, to 87 parts of dry toluene which has been cooled to −70°. The addition takes place at a rate such that the temperature does not go above −60° and at a rate such that the sodium dihydro bis(2-methoxyethoxy)aluminate is added slightly faster that the diester. The addition takes place over a period of about 15 minutes and the reaction then is allowed to stir at −70° for 3½ hours. After that time, the temperature is allowed to rise to 0° and the reaction mixture is stirred at that temperature for 15 additional minutes. Then 4 parts of methanol in 8.7 parts of toluene is added, followed by the addition of 150 parts by volume of 1 N aqueous hydrochloric acid. The aqueous and organic layers which form are separated and the organic layer is washed successively with aqueous potassium bicarbonate and water and dried over anhydrous sodium sulfate. The solvent is stripped under reduced pressure to afford methyl 3-hydroxy-5-oxocyclopent-1-eneheptanoate. That crude product is then dissolved in 222 parts of tetrahydrofuran and treated with 30 parts by volume of a 1 N aqueous hydrochloric acid solution. The total mixture is allowed to stand at about 4° for about 16 hours and then the tetrahydrofuran is removed under reduced pressure. The remaining material is diluted with ethyl acetate, and the organic layer is washed with potassium bicarbonate and water and dried over anhydrous sodium sulfate. The solvent is removed under reduced pressure and the crude material which remains is crystallized from ethyl ether to afford pure methyl 3-hydroxy-5-oxocyclopent-1-eneheptanoate, melting at about 50°–51°.

EXAMPLE 2

222 Parts of redistilled tetrahydrofuran is cooled to 0° and then treated with 15.6 parts by volume of 1M lithium aluminum hydride in tetrahydrofuran. The temperature of that mixture is lowered to −70° and 6.92 parts of methyl 2-methoxy-4-hydroxy-5-oxocyclopent-1-eneheptanoate dissolved in 53 parts of tetrahydrofuran is added. The addition takes place over a 2 minute period and the temperature of the reaction mixture is not allowed to rise above −60°. After the addition is complete, the temperature is lowered to −70° and the reaction mixture is stirred for 4½ hours. Then 4 parts of methanol and 8.9 parts of tetrahydrofuran is added and the temperature of the reaction mixture is allowed to rise to −20° at which time 60 parts by volume of a 1 N hydrochloric acid solution is slowly added. The resulting mixture is allowed to stand for 16 hours at a temperature of about −4°. Then the solvent is removed under reduced pressure and the residue which remains is diluted with ethyl acetate. The aqueous and organic layers which form are separated and the organic layer is washed with water, potassium bicarbonate and water and dried over anhydrous sodium sulfate. After the solvent is removed under reduced pressure, the remaining material is chromatographed on silicic acid with ethyl acetate-benzene (1:4) as eluant to afford methyl 3-hydroxy-5-oxocylopent-1-eneheptanoate.

EXAMPLE 3

A solution of 0.500 part of 2-methoxy-4-hydroxy-5-oxocyclopent-1-eneheptanoic acid dissolved in 25 parts by volume of hexamethyl phosphoramide is treated with 0.094 part of sodium hydride and stirred for 1½ hours. Then 8.5 parts by volume of lithium aluminum hydride is added and the reaction mixture is stirred at room temperature for ½ hour and then heated at 70°–75° for 1¾ hours. The solution is acidified with hydrochloric acid and allowed to stand at room temperature for about 16 hours. Water and chloroform then are added to form 2 layers which are separated. The organic layer is extracted with 5% aqueous sodium carbonate. The sodium carbonate extracts are washed with chloroform and then acidified with hydrochloric acid. The acidified extracts are themselves extracted with ethyl acetate and washed with water, dried over anhydrous sodium sulfate and stripped of solvent. In that manner there is afforded 3-hydroxy-5-oxocyclopent-1-eneheptanoic acid.

EXAMPLE 4

10 Parts of sulfuric acid is treated with 9 parts of 20% fuming sulfuric acid and allowed to stand at room temperature for 10 minutes. 1.25 Parts by volume of that solution then is added dropwise to 28.5 parts by volume of 1M lithium aluminum hydride in tetrahydrofuran. After the addition is complete, the temperature is maintained at −60° for 15 minutes and then allowed to rise to room temperature. The aluminum hydride solution so obtained is cooled to −60° and added rapidly to a solution of 6.92 parts of methyl 2-methoxy-4-hydroxy-5-oxocyclopent-1-eneheptanoate dissolved in 310 parts of redistilled tetrahydrofuran which is cooled to −40°. The temperature is lowered to −70° after the addition is complete and the reaction mixture is stirred at that temperature for 3¾ hours. Then 7.9 parts of methanol in 17.8 parts of tetrahydrofuran is added slowly and the temperature is allowed to rise to −20° at which time 120 parts by volume of a 1 N aqueous hydrochloric acid solution is added. The mixture is allowed to stand at about 4° for 16 hours and then the solvent is removed under reduced pressure. The aqueous residue which remains is diluted with ethyl acetate and the organic and aqueous layers separated. The organic layer is washed with water, potassium bicarbonate and water. Then it is dried over anhydrous sodium sulfate and the solvent is removed under reduced pressure to afford methyl 3-hydroxy-5-oxocyclopent-1-eneheptanoate.

EXAMPLE 5

By substituting an equivalent quantity of ethyl 2-ethoxy-4-hydroxy-5-oxocyclopent-1-eneheptanoate in the procedure of Example 1, there is afforded ethyl 3-hydroxy-5-oxocyclopent-1-eneheptanoate.

EXAMPLE 6

When an equivalent quantity of lithium borohydride is substituted in the procedure of Example 2, there is afforded methyl 3-hydroxy-5-oxocyclopent-1-eneheptanoate.

EXAMPLE 7

Substitution of an equivalent quantity of methyl 2-methoxy-4-hydroxy- 5-oxocyclopent-1-eneoctanoate in the procedure of Example 1 affords methyl 3-hydroxy-5-oxocyclopent-1-eneoctanoate.

EXAMPLE 8

A solution of 10.0 parts of methyl 2-methoxy-4-hydroxy-5-oxocyclopent-1-eneheptanoate in 450 parts of redistilled tetrahydrofuran is cooled to −39°. To the stirred solution, under a nitrogen atmosphere, is added rapidly 65.7 parts by volume of a 0.564 M borane in tetrahydrofuran solution. The reaction mixture is stirred for 2½ hours at −40° and 248 parts of acetone is added. The solution is stirred for an additional hour, then acidified with dilute aqueous hydrochloric acid and allowed to warm to room temperature. After standing for 16 hours at room temperature, the acetone and tetrahydrofuran are removed by warming to 40° and the remaining material is extracted with ethyl acetate. The ethyl acetate extract is washed with dilute potassium carbonate and dried over anhydrous sodium sulfate. Then the solvent is removed under reduced pressure and the crude product is chromatographed on silicic acid and eluted with 1:4 ethyl acetate-benzene, thus yielding methyl 3-hydroxy-5-oxocyclopent-1-eneheptanoate.

EXAMPLE 9

A mixture of 0.240 part of methyl 3-hydroxy-5-oxocyclopent-1-eneheptanoate, 10 parts by volume of 0.1 N sodium hydroxide and 7.9 parts of methanol is allowed to stand at room temperature for 16 hours, then diluted with water and extracted with ethyl acetate. The aqueous layer is acidified with 1 N hydrochloric acid and then extracted with ethyl acetate. The ethyl acetate extract is washed with water, dried over anhydrous sodium sulfate and stripped of solvent under reduced pressure. Chromatography of the crude product on silica gel with 50% ethyl acetate-benzene affords 3-hydroxy-5-oxocyclopent-1-eneheptanoic acid, melting at about 47°–48.5°. That compound is characterized further by absorption in the ultravoilet spectrum at about 222 millimicrons with a molecular extinction coefficient of about 7700 and a maximum in the nuclear magnetic resonance spectrum at about 87.2 ppm.

EXAMPLE 10

To a stirred solution of 200 parts by volume of 1 M borohydride in tetrahydrofuran at 0° under a nitrogen atmosphere is added, dropwise over a 30 minute period, 22 parts of catechol in 44 parts of tetrahydrofuran. That solution is stirred at room temperature for 1 hour. Then 16 parts of 1-hexyne is added and the solution is refluxed for 2 hours. The reaction mixture is cooled to 0° and treated with 54 parts of mercuric chloride. The resulting mixture is stirred at 0° for 1 hour and allowed to warm to room temperature. After standing at room temperature for 16 hours, the mixture is poured into a 3:1 water-acetone mixture and the white precipitate which forms is collected and washed with water. Then the precipitate is dissolved in boiling hexane and the solution is filtered while hot and cooled to 0° to afford white crystals of trans-1-hexenyl mercuric chloride, melting at about 111°.

EXAMPLE 11

When an equivalent quantity of 1-octyne is substituted in the procedure of Example 8, there is produced trans-1-octenyl mercuric chloride, melting atabout 104°–105°.

EXAMPLE 12

A suspension of 1.6 parts of magnesium powder and 27 parts of tetrahydrofuran, distilled from an ethyl magnesium bromide solution, is treated with 1 part of mercuric chloride. After stirring the mixture for 15 minutes, 5.1 parts of trans-1-hexenyl mercuric chloride is added and that mixture is stirred for about 16 hours at room temperature. The supernatant is decanted from the excess magnesium and then stirred and cooled to −60° in an isopropanol/dry ice bath. Then 3.0 parts of cuprous iodide is added in one portion and the mixture is allowed to warm to −30°, at which temperature it is held for 10 minutes. The mixture is cooled to −60° and 1.47 parts of methyl 3-hydroxy-5-oxocyclopent-1-eneheptanoate, dissolved in tetrahydrofuran, is added dropwise to the reaction mixture. That mixture is stirred for 30 minutes and then poured into a mixture consisting of 140 parts of ethyl ether and 100 parts by volume of aqueous 0.5 N hydrochloric acid. The ether layer is separated, washed with water and dried over anhydrous sodium sulfate. Then the solvent is removed under reduced pressure and the material remaining is dissolved in 40 parts of acetone containing 10 parts by volume of 1 N aqueous hydrochloric acid. That mixture is allowed to stand at room temperature for one hour and then it is diluted with water and extracted with ether. The ether extract is washed with water, dried over anhydrous sodium sulfate and stripped of solvent. The residue which remains is chromatographed on silica gel using ethyl acetate and benzene as eluant to give racemic methyl 2α-(1-hexenyl)-3α-hydroxy-5-oxocyclopentane-1α-heptanoate, racemic methyl 2α-(1-hexenyl)-3α-hydroxy-5-oxocyclopentane-1β-heptanoate and racemic methyl 2β-(1-hexenyl)-3α-hydroxy-5-oxocyclopentane-1β-heptanoate as yellow oils. Those compounds display absorption maxima in the infrared spectrum at about 1744 reciprocal centimeters.

EXAMPLE 13

When equivalent quantities of trans-1-octenyl mercuric chloride and methyl 3-hydroxy-5-oxocyclopent-1-eneheptanoate are substituted in the procedure of Example 12, there is produced racemic methyl 2α-(1-octenyl)-3α-hydroxy-5-oxocyclopentane-1β-heptanoate, racemic methyl 2β-(1-octenyl)-3α-hydroxy-5-oxocyclopentane-1α-heptanoate and racemic methyl 2β-(1-ocetenyl)-3α-hydroxy-5-oxocyclopentane-1β-heptanoate. Those materials appear as yellow oils.

What is claimed is:

1. The process of producing a compound of the formula

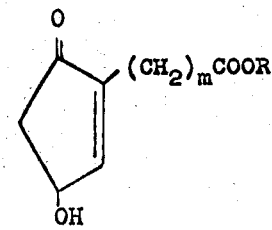

which comprises contacting, in an inert solvent at a temperature between about −90° to +10°C., a compound of the formula

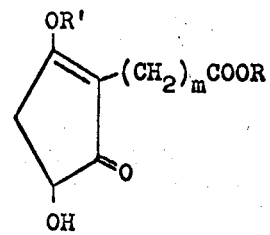

wherein R is lower alkyl, R' is lower alkyl, (lower alkoxy) lower alkoxy and $m$ is an integer greater than 4 and less than 8 with a hydride reducing agent selected from compounds of the formula

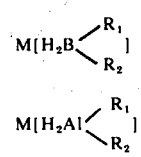

wherein M is an alkali metal and $R_1$ and $R_2$ are hydrogen, lower alkyl or lower alkoxy, or from aluminum hydride, borane or zinc borohydride, to form, as an unisolated intermediate, a compound of the formula

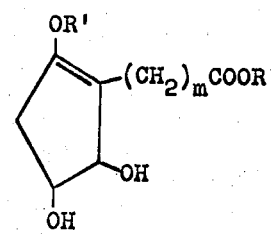

and contacting, at about the same temperature, said unisolated intermediate with an acidic agent comprising a mineral acid or a strong organic acid.

2. The process of claim 1, wherein the hydride reducing agent is aluminum hydride, lithium aluminum hydride, sodium dihydro bis(2-methoxyethoxy)-aluminate, sodium borohydride or borane and the acidic agent is an aqueous mineral acid.

3. The process of claim 1, wherein $m$ is the integer 6, R' is methyl, the hydride reducing agent is aluminum hydride, lithium aluminum hydride or sodium dihydro bis(2-methoxyethoxy)aluminate and the acidic agent is an aqueous mineral acid.

4. The process of claim 1, wherein *m* is the integer 6, R' is methyl, the hydride reducing agent is sodium bis(methoxyethoxy)aluminate and the acidic agent is aqueous hydrochloric acid.

5. The process of claim 1, wherein *m* is the integer 6, R and R' are methyl, the hydride reducing agent is sodium dihydro bis(methoxyethoxy)aluminate and the acidic agent is aqueous hydrochloric acid.

6. The process of producing a compound of the formula

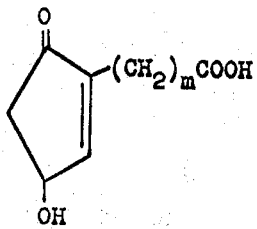

which comprises contacting, in an inert solvent, a compound of the formula

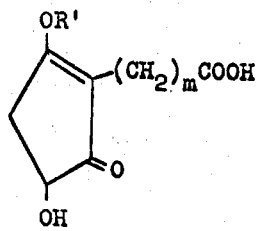

wherein R' is lower alkyl, (lower alkoxy) lower alkoxy and *m* is an integer greater than 4 and less than 8, with a hydride reducing agent selected from compounds of the formula

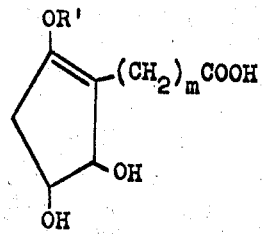

wherein M is an alkali metal and $R_1$ and $R_2$ are hydrogen, lower alkyl or lower alkoxy, or from aluminum hydride, borane or zinc borohydride, to form, as an unisolated intermediate, a compound of the formula

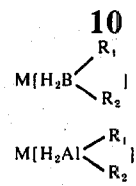

and contacting said unisolated intermediate with an acidic agent comprising a mineral acid or a strong organic acid.

7. The process of claim 6 wherein the hydride reducing agent is aluminum hydride, lithium aluminum hydride, sodium dihydro bis(2-methoxyethoxy)aluminate, sodium borohydride or borane and the acidic agent is an aqueous mineral acid.

8. The process of claim 6 wherein the hydride reducing agent is aluminum hydride, lithium aluminum hydride or sodium dihydro bis(2-methoxyethoxy)aluminate and the acidic agent is an aqueous mineral acid.

9. The process of claim 6 wherein the hydride reducing agent is sodium dihydro bis(2-methoxyethoxy)aluminate, *m* is the integer 6 and the acidic agent is aqueous hydrochloric acid.

10. The process of claim 6 wherein the hydride reducing agent is sodium dihydro bis(2-methoxyethoxy)aluminate, R' is methyl, *m* is the integer 6 and the acidic agent is aqueous hydrochloric acid.

* * * * *